United States Patent [19]

Otsuka et al.

[11] Patent Number: 5,344,650
[45] Date of Patent: Sep. 6, 1994

[54] AQUEOUS COSMETIC COMPOSITION AND PREPARATION METHOD THEREOF

[75] Inventors: Noriko Otsuka, Koshigaya; Ichiro Tokimitsu, Tokyo, both of Japan

[73] Assignee: Kao Corporation, Tokyo, Japan

[21] Appl. No.: 22,394

[22] Filed: Feb. 24, 1993

Related U.S. Application Data

[63] Continuation of Ser. No. 746,989, Aug. 19, 1991, abandoned.

[30] Foreign Application Priority Data

Aug. 31, 1990 [JP] Japan ................................ 229877

[51] Int. Cl.$^5$ .............................................. A61K 6/00
[52] U.S. Cl. ................................... 424/401; 424/70; 424/71; 424/63
[58] Field of Search .................. 424/401, 63, 70, 71; 514/785, 772, 941

[56] References Cited

U.S. PATENT DOCUMENTS

| | | | |
|---|---|---|---|
| 4,348,415 | 9/1982 | Tsutsumi et al. | 514/785 |
| 4,370,319 | 1/1983 | Chapin et al. | 514/772 |
| 5,028,416 | 7/1991 | Yano et al. | 424/401 |

FOREIGN PATENT DOCUMENTS

| | | |
|---|---|---|
| 015030 | 9/1980 | European Pat. Off. |
| 028457 | 5/1981 | European Pat. Off. |
| 277641 | 8/1988 | European Pat. Off. |
| 391124 | 10/1990 | European Pat. Off. |

Primary Examiner—Thurman K. Page
Assistant Examiner—William E. Benston, Jr.
Attorney, Agent, or Firm—Oblon, Spivak, McClelland, Maier & Neustadt

[57] ABSTRACT

An emulsion-type aqueous cosmetic composition comprising:

(i) a mixture of oil and fat, wherein said fat is present in at least 70 wt. % of said mixture, and at least 50 wt. % of said fat is at least one lipid selected from the group consisting of higher fatty acids, cholesterol, cholesterol fatty acid esters, ceramides, sugar ceramides, and compounds having the following formula (I):

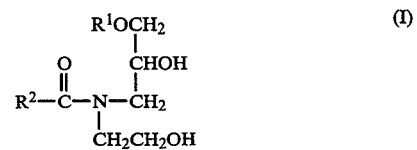

wherein $R^1$ is a linear or branched, saturated or unsaturated hydrocarbon group having 10 to 26 carbon atoms, and $R^2$ is a linear or branched, saturated or unsaturated hydrocarbon group having 9 to 25 carbon atoms, (ii) an aqueous medium, and
(iii) an emulsifying agent, said mixture of oil and fat being dispersed in said aqueous medium with said emulsifying agent.

12 Claims, No Drawings

AQUEOUS COSMETIC COMPOSITION AND PREPARATION METHOD THEREOF

This application is a continuation of application Ser. No. 07/746,989, filed on Aug. 19, 1991, now abandoned.

BACKGROUND OF THE INVENTION

Field of the Invention

The present invention relates to an emulsion-type aqueous cosmetic composition which exhibits excellent dispersion stability, provides excellent skin-care and moisturizing effects, and imparts a pleasant feeling to users thereof, and to a method of preparing a cosmetic composition having improved dispersion stability.

Description of the Background Art

A cosmetic composition prepared by dispersing oil and fat in an aqueous medium, which is called a "lotion" or "milky lotion", is used for purposes of moisturizing and softening the skin, improving the appearance of the skin, and the like. The terms "oil" and "fat" refer to liquid oil and solid fat, examples of which are hydrocarbons, higher fatty acids and esters thereof. In general, a cosmetic composition of the above type is prepared by emulsifying a mixture of oil and fat, mainly containing liquid oil, with a surface active agent. The cosmetic composition therefore displays acceptable dispersion stability, but when additional components are added to provide satisfactory skin-moisturizing and softening properties, the composition subsequently feels sticky and/or greasy. The sticky and/or greasy feel to the cosmetic composition can be eliminated by the use of an increased amount of solid fat. However, a cosmetic composition containing a large amount of solid fat exhibits low dispersion stability.

SUMMARY OF THE INVENTION

Accordingly, it is an object of the present invention to provide a cosmetic composition which displays excellent dispersion stability.

It is a further object of the present invention to provide a cosmetic composition which exhibits excellent skin care and skin moisturizing effects.

These and other objects, which will become apparent during the course of the following detailed description of the present invention have been realized by an emulsion-type aqueous cosmetic composition comprising (i) a mixture of oil and fat, wherein said fat is present in at least 70 wt. % of said mixture, and at least 50 wt. % of said fat is at least one lipid selected from the group consisting of higher fatty acids, cholesterol, cholesterol fatty acid esters, ceramides, sugar ceramides, and compounds having the following formula (I):

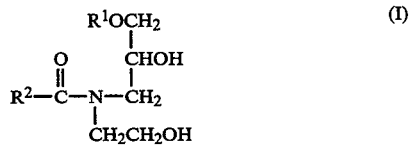

(I)

wherein
R$^1$ is a linear or branched, saturated or unsaturated hydrocarbon group having 10 to 26 carbon atoms, and
R$^2$ is a linear or branched, saturated or unsaturated hydrocarbon group having 9 to 25 carbon atoms, (ii) an aqueous medium, and (iii) an emulsifying agent, the oil and fat being dispersed in the aqueous medium with the emulsifying agent, and a method for the preparation of a cosmetic composition exhibiting high dispersion stability.

DETAILED DESCRIPTION OF THE PREFERRED EMBODIMENTS

In the present specification, the terms "oil" and "fat" refer to liquid oil and solid fat, respectively. Suitable examples are hydrocarbons, higher fatty acids and esters thereof, higher fatty alcohols, and the like, which are generally used for cosmetics, excluding silicone-type oily agents. A liquid oil is an oil which is liquid at room temperature (25° C.).

A fatty acid is defined as a carboxylic acid of from 10 to 30 carbon atoms, which may have one or more substituents, and may be saturated or have one, two, three or more sites of unsaturation (carbon-carbon double bonds), which in turn, may be of either cis or trans configuration. Examples of fatty acids are myristic acid, palmitic acid, stearic acid, oleic acid, behenic acid, lauric acid, linoleic acid, linolenic acid, erucic acid, arachidonic acid, arachidic acid, levulenic acid and eleostearic acid.

Examples of liquid oils suitable for use in the present composition include hydrocarbons such as liquid paraffin, mineral oil, squalane and petroleum jelly; liquid esters of fatty acids, such as lower alcohol esters of fatty acids, for example isopropyl myristate, neopentyl glycol esters of fatty acids, and fatty acid esters found in jojoba oil and whale oil; glycerides of fatty acids, such as those found in olive oil, soybean oil, castor oil, vegetable oil, peanut oil, sunflower oil and macadamia nut oil; liquid acetate esters of fatty alcohols; and other oils, such as aloe, and vitamins, such as Vitamin E, Vitamin E acetate, and Vitamin K.

The solid fat is a fat which is solid at room temperature (25° C.). Examples of solid fats suitable for use in the present composition include solid hydrocarbons, such as paraffin wax and/or other solid hydrocarbons of from 20 to 50 carbon atoms, which may be saturated or unsaturated, straight-chain or branched; wax esters such as beeswax; other solid fatty acid esters of alcohols having form 1 to 24 carbon atoms; solid glycerides of fatty acids, such as cacao fat; higher fatty alcohols such as cetanol (hexadecanol), dodecanol, tetradecanol, octadecanol, eicosanol and oleyl alcohol; and mixtures thereof.

In the present invention, the term "lipid" refers to a group of substances, which are found between corneocytes or analogues of them synthesized chemically between corneocytes, and form a lamellar structure in water, either singly or in combination. These substances are solid at room temperature, and are an example of suitable solid fats. More specifically, lipids found between corneocytes are fatty acids, cholesterol, cholesterol fatty acid esters, ceramides and sugar ceramides. Particularly preferable synthetic substances analogous to ceramides are lipid derivatives containing two long chain hydrocarbon groups joined by a linking unit therebetween, the linking unit having at least one OH group and an amide group, and can adopt a planar conformation. Preferably, the linking unit is a 2-oxyethylaminocarbonyl derivative or a 3-oxypropylaminocarbonyl derivative, particularly preferably a 2-hydroxy-3-oxypropyl-aminocarbonyl linking unit. An amide derivative having the following formula (I), which is disclosed in Japanese Laid-Open Patent Application No. 62-228048, European Patent Application Nos. 227,991-A (Jul. 8, 1987) and 227,994-B (Sep. 13, 1989), and German Patent No. 3,665,580 is one example of the analogues of ceramides:

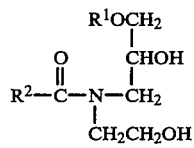

wherein $R^1$ is a linear or branched, saturated or unsaturated hydrocarbon group having 10 to 26 carbon atoms, preferably 12 to 22 carbon atoms, particularly preferably 14 to 18 carbon atoms, and $R^2$ is a linear or branched, saturated or unsaturated hydrocarbon group having 9 to 25 carbon atoms, preferably 11 to 21 carbon atoms, particularly preferably 13 to 17 carbon atoms. Preferably $R^1$ and $R^2$ are linear. Also, $R^1$ and $R^2$ are preferably saturated.

Examples of the cholesterol fatty acid esters include fatty acid esters of cholesterol wherein the fatty acid is saturated or unsaturated, linear or branched, and containing 8 to 20 carbon atoms, preferably 10 to 18 carbon atoms, particularly preferably 12 to 16 carbon atoms. Of these fatty acid esters, a branched fatty acid ester of cholesterol is preferred, particularly where the fatty acid contains one or more lower alkyl substituents, such as a methyl group, an ethyl group, and the like.

The above-described oils and fats can be used either singly or in combination thereof. Any amount of oil and fat which results in a stable aqueous dispersion is suitable for the present composition. However, the amount of oil and fat incorporated into the present composition is preferably from 0.5 to 30 wt. % of the total weight of the aqueous cosmetic composition of the invention, more preferably 0.5 to 20 wt. %, particularly preferably form 1 to 15 wt. %. In the present invention, a mixture of oil and fat which contains a proportion of at least 70 wt. % of solid fat is used, and at least 50% of the solid fat is one or more lipids selected from the group consisting of higher fatty acids, cholesterol, cholesterol fatty acid esters, ceramides, sugar ceramides, and compounds having the following formula (I):

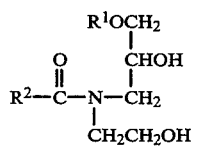

wherein
$R^1$ is a linear or branched, saturated or unsaturated hydrocarbon group having 10 to 26 carbon atoms, and
$R^2$ is a linear or branched, saturated or unsaturated hydrocarbon group having 9 to 25 carbon atoms. It is particularly preferable that the solid fat contain at least 70% of at least one lipid, in order to enhance the dispersion stability and the skin-moisturizing effect of the composition. Furthermore, in order to enhance the skin-moisturizing effects, it is preferred that the amount of the lipid ( s ) contained in the cosmetic composition be in the range of from 2% to 20%, particularly from 3% to 10%.

A conventional emulsifying agent may be employed in the cosmetic composition of the present invention. Examples of conventional emulsifying agents include nonionic, anionic, cationic and amphoteric surface active agents. The use of a combination of a hydrophilic surface active agent and an oleophilic surface active agent is acceptable. However, a phosphate ester anionic surface active agent, and in particular, a polyoxyethylene alkyl ether phosphoric acid ester surface active agent having the following formula (II) is preferred when considering dispersion stabilizing effects and skin-irritating properties of the composition:

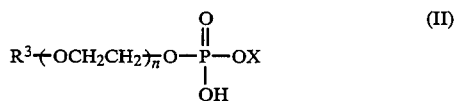

wherein $R^3$ is a hydrocarbon group having 8 to 36 carbon atoms, preferably 10 to 30 carbon atoms, particularly preferably 12 to 22 carbon atoms, n is a number of 1 to 0 on the average, preferably 1 to 5, particularly preferably 1 to 3, and X is an inorganic or organic cation, preferably an alkali metal (for example, sodium, potassium and lithium), an alkaline earth metal (calcium and magnesium) ammonium, or ammonium substituted with from 1 to 4 alkyl groups of from 1 to 20 carbon atoms, which may be further substituted with a phenyl group; e.g., benzyltrimethylammonium or dodecyltriethylammonium.

It is preferable that the incorporation amount of the above emulsifying agent be in the range of from 0.5 wt. % to 5 wt. % of the total weight of the cosmetic composition of the invention, particularly from 1 to 3 wt. %.

Examples of suitable aqueous media usable in the present invention include water; a mixture of water and a water-soluble monohydric alcohol, preferably a lower alcohol, such as methanol, ethanol, propanol, isopropanol and butanol; and a mixture of water and a water-soluble polyhydric alcohol such as ethylene glycol, glycerin, propylene glycol, 1,2-propanediol, 1,2-, 1,3- and 2,3-butanediol, and butylene glycol (1,4-butanediol). The aqueous medium generally comprises the balance of the composition after the presence of all other components has been considered; however, the aqueous medium is preferably incorporated in an amount of from 60 wt. % to 95 wt. % of the total weight of the cosmetic composition of the present invention.

In addition to the above essential components, other auxiliary components such as a silicone-type oily agent, a humectant or moisturizing agent such as a polysaccharide, and absorption promoting agent for the lipid(s), an ultraviolet absorbing agent, a chelating agent, a pH modifier, an antiseptic, a colorant, a perfume, a viscosity modifier, and the like can be incorporated into the cosmetic composition of the present invention, unless they mar the beneficial effects of the invention.

In particular, the incorporation of a silicone-type oily agent is recommended, because a silicone-type oily agent reduces the greasiness of the composition, and imparts a refreshing feeling to users. Examples of silicone-type oily agents suitable for use in the present invention are dimethylpolysiloxanes, methylphenylpolysiloxanes, cyclic silicones, such as hexamethyltrisiloxane, octamethyltetrasiloxane, decamethylpentasiloxane and dodecamethylhexasiloxane, and mixtures thereof. The amount of the silicon-type oily agent incorporated into the present composition is preferably from 0.1 wt. % to 10 wt. % of the total weight of the present cosmetic composition, particularly preferably from 0.5 to 7 wt. %.

Glyceryl ethers are preferably incorporated into the present composition as absorption promoting agents for the lipid. Typical examples of the glyceryl ethers suitable for use in the present composition are compounds represented by the following formula (III):

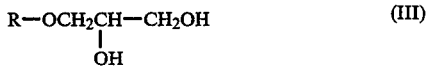

wherein R is an alkyl group having 8 to 24 carbon atom, preferably having 12 to 22 carbon atoms. Of the glyceryl ethers (III), particularly preferable ones are those compounds whose R is a group represented by the following formula (IV):

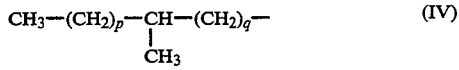

wherein p is an integer of from 4 to 10, and q is an integer of from 5 to 11, provided that the total number of p and q is from 11 to 17, and the distribution of p and q is at its maximum when p is 7 and q is 8.

The cosmetic composition of the present invention is preferably prepared in the following manner:

The oil and fat, the emulsifying agent, and a small portion of the aqueous medium mixed at a temperature of 60° to 80° C. to give a uniform solution. To the solution, the remaining aqueous medium is added and mixed, followed by conventional emulsification to obtain the desired cosmetic composition.

More specifically, in the method of the present invention, the mixture of oil and fat and the emulsifying agent in their entireties are mixed with a small portion of the aqueous medium, and the resulting preliminary mixture is heated to a temperature of 60° to 80° C. to give a solution. The small amount of the aqueous medium used in the preliminary mixing process step is preferably as small as from about 0.1 to 5% of the whole quantity of the aqueous medium used in the composition, particularly preferably from 0.3 wt. % to 4 wt. %. Further, to obtain a uniform solution, it is preferable to add, apart from the aqueous medium, from 0.5% to 10% of a water-soluble polyhydric alcohol, such as ethylene glycol, glycerin, propylene glycol, 1,2-propanediol, 1,2-, 1,3- and 2,3-butanediol and butylene glycol, to the preliminary mixture, and to thoroughly stir the mixture. Subsequently, the remainder of the aqueous medium is added to the above solution, and the mixture is emulsified by stirring or sonification, preferably by stirring. The resulting emulsion is then cooled to obtain the cosmetic composition of the present invention having a high dispersion stability.

Although any viscosity is suitable as long as a high degree of dispersion stability is ascertained, it is preferable to adjust the viscosity of the cosmetic composition to 3000 cps or less, particularly preferably to 2500 cps or less. A cosmetic composition having such a viscosity imparts a pleasant feeling to users thereof.

Furthermore, the above procedure is not limited to the present composition. It is within the scope of the present invention to provide a method for increasing the dispersion stability of any emulsion comprising oil and/or fat, and aqueous medium, and a conventional emulsifying agent. The present method clearly results in surprising improvements in the dispersion stability of an oil and/or fat-in-water emulsion, as evidenced by the results presented below.

As described above, the present invention provides an emulsion-type aqueous cosmetic composition comprising a large amount of the lipids, which exhibits excellent moisturizing effects and dispersion stability, and imparts a pleasant feeling to users.

Other features of this invention will become apparent in the course of the following description of exemplary embodiments, Which are given for illustration of the invention and are not intended to be limiting thereof.

EXAMPLES 1-2 AND COMPARATIVE EXAMPLES 1-2

Milky lotions having the formulations shown in Table 1 below were prepared, and the moisturizing effect and the retentivity of the moisturizing effect were evaluated.

TABLE 1

| | AMOUNTS (WT. %) | | | |
| | Present Examples | | Comparative Examples | |
| Component | 1 | 2 | 1 | 2 |
|---|---|---|---|---|
| 1 Ceramide-analogous material (In formula (I), $R^1 = C_{16}H_{33}$, $R^2 = C_{15}H_{31}$) | 3.0 | — | 0.3 | — |
| 2 Cholesterol | 1.0 | 1.0 | 0.1 | 0.1 |
| 3 Sugar ceramide* | — | 3.0 | — | 0.3 |
| 4 Glyceryl ether | 0.5 | 0.5 | 0.5 | 0.5 |
| 5 Squalane | 0.5 | 0.5 | 0.5 | 0.5 |
| 6 Silicone oil** | 2.0 | 2.0 | 2.0 | 2.0 |
| 7 Sodium lauryl polyoxyethylene ether phosphate (4EO)*** | 1.5 | 1.5 | 1.5 | 1.5 |
| 8 Sorbitan monostearate | 0.5 | 0.5 | 0.5 | 0.5 |
| 9 Glycerin | 5.0 | 5.0 | 5.0 | 5.0 |
| 10 Ethanol | 10.0 | 10.0 | 10.0 | 10.0 |
| 11 Purified water | balance | balance | balance | balance |

Note)
*Manufactured by Sigma Corporation
**SILICONE KF-96A" (Trademark) (6 cs), manufactured by Shin-Etsu Chemical Co., Ltd.
***Containing four ethyloxy units

Preparation Method

The oily agents (components 4 and 5 shown in Table 1), the fats (Components 1-3), the emulsifying agents (Components 7 and 8), the silicone-type oil (Component 6), glycerin (Component 9), and 1.0 wt. % of the whole quantity of purified water (Component 11) were mixed, and the resulting preliminary mixture was heated to a temperature of 70° C. to obtain a solution. The remaining aqueous media (ethanol (Component 10) and the remainder of the purified water) were gradually added to the solution, while maintaining the solution at the 70° C. temperature, followed by emulsification by using a conventional emulsifier. The emulsion thus obtained was cooled to 25° C. by a conventional heat exchanger, whereby milky lotions (Present Examples 1 and 2) were respectively prepared. Comparative compositions 1 and 2 were also prepared in the same manner above.

Test Method

A predetermined amount of each of the above-prepared milky lotions was applied to the inner part of the forearm of a subject. After three hours, the forearm was washed with hot water, and the subject entered a conventional thermohygrostatic chamber maintained at a temperature of 20° C. and a relative humidity of 50% for 30 minutes. The water content in the horny layer of the skin (the stratum corneum epidermis) was then measured by an impedance meter (manufactured by IBS Corporation) to evaluate the moisturizing effects. After three hours, the forearm was washed again with hot water. The subject reentered the thermo-hygrostatic chamber maintained at 20° C. and 50% RH for 30 minutes, after which the water content in the horny layer of the skin was measured again by the impedance meter to evaluate the retentivity of the moisturizing effects. The above test was repeated five times. Shown in Table 2 are the averages of the values obtained in the above tests.

TABLE 2

| Test | Present Examples | | Comparative Compositions | |
|---|---|---|---|---|
| | 1 | 2 | 1 | 2 |
| Moisturizing effect | 45 | 38 | 16 | 13 |
| Retentivity of moisturizing effect | 40 | 35 | 9 | 8 |

(unit: $\mu\Omega^{-1}$)

As is clear from the data shown in the above table, the milky lotions of the present invention exhibit excellent moisturizing effects and excellent retentivity of the moisturizing effects.

EXAMPLE 3 AND COMPARATIVE COMPOSITION 3

Milky lotions having the formulations shown in Table 3 below were prepared, and the preservation of the dispersion stability was evaluated for each composition prepared.

TABLE 3

AMOUNTS (WT. %)

| Component | Present Example No. 3 | Comparative Composition No. 3 |
|---|---|---|
| 1 Ceramide-analogous material (In formula (I), $R^1 = C_{16}H_{33}$, $R^2 = C_{15}H_{31}$) | 5.0 | — |
| 2 Stearic acid | 1.0 | 1.0 |
| 3 Solid paraffin | — | 5.0 |
| 4 Olive oil | 0.5 | 0.5 |
| 5 Cetanol | 0.5 | 0.5 |
| 6 Glyceryl ether (In formula (IV), p = 7, q = 8) | 0.3 | 0.3 |
| 7 Silicone oil* | 3.0 | 3.0 |
| 8 Arginine 2-hexadecyl phosphate | 2.0 | 2.0 |
| 9 Polyoxyethylene hydrogenated castor oil | 0.5 | 0.5 |
| 10 Sorbitol | 7.0 | 7.0 |
| 11 1,3-Butylene glycol | 5.0 | 5.0 |
| 12 Purified water | balance | balance |

Note)
*"SILICONE SH200" (Trademark) (100 cs), manufactured by Toray Silicone Co., Ltd.

Preparation Method

The fats (Components 1 and 2 shown in Table 3), the oily agents (Components 4–6), the emulsifying agents (Components 8 and 9), sorbitol (Component 10), and 0.5% of the entire quantity of purified water (Component 12) shown in Table 3 were mixed, and the resulting mixture was heated to a temperature of 70° C. to obtain a solution. The remaining aqueous media (1,3-butanediol (Component 11) and the remaining purified water) to the solution were gradually added while maintaining the solution at 70° C., followed by emulsification by using a conventional emulsifier. The emulsion thus obtained was cooled to 25° C. by a conventional heat exchanger, whereby a milky lotion (Present Example 3) was prepared. Comparative Composition No. 3 was also prepared in the same manner as above.

Further, a composition having the same formulation as that of Example 3 of the present invention was prepared in the following comparative manner:

Namely, Components 1–9 were mixed, and the resulting mixture was heated to a temperature of 70° C. to obtain a solution. To the solution was gradually added a mixture of the aqueous media (Components 10 to 12) while maintaining the solution at 70° C., followed by emulsification by using a conventional emulsifier. The emulsion thus obtained was cooled to 25° C. by a conventional heat exchanger, whereby a milky lotion was obtained.

Test Method

The above-obtained three milky lotions were preserved in a conventional thermostatic bath maintained at a temperature of 50° C. The lotions were visually observed after 10 days, 20 days, and 30 days, respectively, and the dispersion of each composition was evaluated. The results are presented in Table 4 below.

TABLE 4

| | Present Example No. 3 | Composition Prepared in Comparative Manner | Comparative Composition No. 3 |
|---|---|---|---|
| After 10 days | ○ | ○ | X |
| After 20 days | ○ | Δ | X |
| After 30 days | ○ | X | X |

Note)
○ No separation of dispersion observed
Δ Slight separation of dispersion observed
X Complete separation of dispersion observed As is clear form the data shown in Table 4 above, the milky lotion according to the present invention displays excellent dispersion stability, superior to those of Comparative Composition No. 3 and the composition prepared in the Comparative Manner.

EXAMPLE 3

Milky lotions having the formulations shown in Table 5 below were prepared, and a panel of ten experts evaluated the compositions organoleptically in terms of the feeling imparted by the composition tested.

TABLE 5

AMOUNTS (WT. %)

| Component | Present Examples | | Comparative Compositions | |
|---|---|---|---|---|
| | 4 | 5 | 4 | 5 |
| 1 Ceramide* | 6.0 | — | — | 6.0 |
| 2 Cholesterol isostearate | — | 6.0 | — | — |
| 3 Palmitic acid | 3.0 | — | — | 3.0 |
| 4 Cholesterol | — | 3.0 | — | — |
| 5 Vaseline | — | — | 6.0 | 6.0 |
| 6 Liquid paraffin | — | — | 3.0 | 3.0 |

TABLE 5-continued

| | | AMOUNTS (WT. %) | | | |
|---|---|---|---|---|---|
| | | Present Examples | | Comparative Compositions | |
| | Component | 4 | 5 | 4 | 5 |
| 7 | Stearyl alcohol | 1.0 | 1.0 | 1.0 | 1.0 |
| 8 | Silicone oil** | 5.0 | 5.0 | 5.0 | 5.0 |
| 9 | Sodium monohexadecyl phosphate | 2.0 | 2.0 | 2.0 | 2.0 |
| 10 | Glyceryl monostearate | 0.5 | 0.5 | 0.5 | 0.5 |
| 11 | Glycerin | 10.0 | 10.0 | 10.0 | 10.0 |
| 12 | Ethanol | 20.0 | 20.0 | 20.0 | 20.0 |
| 13 | Purified water | balance | balance | balance | balance |

Note)
*Manufactured by Sigma Corporation
**"SILICONE SH-344" (Trademark), manufactured by Toray Silicone Co., Ltd.

Preparation Method

The fats (Components 1 and 3 or Components 2 and 4 shown in Table 5), the oil agents (Component 7), the silicone-type oil (Component 8), the emulsifying agents (Components 9 and 10), glycerin (Component 11), and 1.5 wt. % of the entire quantity of purified water (Component 13) recited in Table 5 above were mixed, and the resulting mixture was heated to a temperature of 70° C. to obtain a solution. The remaining aqueous media (ethanol (Component 12) and the remainder of the purified water) were gradually added to the solution while maintaining the solution at 70° C., followed by emulsification by using a conventional emulsifier. The emulsion thus obtained was cooled to 25° C. by a conventional heat exchanger, whereby milky lotions (Examples 4 and 5 of the present invention) were respectively prepared. Comparative compositions 4 and 5 were also prepared in the same manner as the above.

Test Method

Ten professional panelists applied the above-obtained milky lotions onto their skin, and organolepically evaluated them in terms of greasiness and stickiness. The results of the tests are presented follows:
⊙: 8 or more panelists among 10 answered "excellent" (neither greasy nor sticky)
○: 6 or 7 panelists answered "excellent"
Δ: 4 or 5 panelists answered "excellent"
X: less than 4 panelists answered "excellent"
Results:

TABLE 6

| | Present Examples | | Comparative Compositions | |
|---|---|---|---|---|
| Organoleptic Test | 4 | 5 | 4 | 5 |
| Greasiness | ⊙ | ○ | X | X |
| Stickiness | ○ | ○ | Δ | X |

As is clear from the data shown in the above table, the milky lotions according to the present invention are neither greasy nor sticky, and impart a pleasant feeling to users thereof.

EXAMPLE 6

A milky lotion having the formulation shown in Table 7 below was prepared.

TABLE 7

| Component | Example 6 (wt. %) |
|---|---|
| 1 Ceramide-analogous material | 6.0 |

TABLE 7-continued

| Component | Example 6 (wt. %) |
|---|---|
| (In formula (I), $R^1 = C_{16}H_{33}$, $R^2 = C_{15}H_{31}$) | |
| 2 Cholesterol | 1.0 |
| 3 Cholesterol isostearate | 1.0 |
| 4 Glyceryl ether | 1.0 |
| (In formula (IV), p = 7, q = 8) | |
| 5 Sodium lauryl polyoxyethylene-ether phosphate (4EO)* | 2.5 |
| 6 Glycerin | 2.0 |
| 7 Sorbitol | 3.0 |
| 8 Purified water | balance |

*Containing four ethyloxy units

Preparation Method

The fats (Components 1-3 shown in Table 7), oily agents (Component 4), the emulsifying agent (Component 5), glycerin (Component 6), sorbitol (Component 7), and 3.0 wt. % of the quantity of purified water (Component 8) recited in Table 7 above were mixed, and the resulting mixture was heated to a temperature of 70° C. to obtain a solution. The remaining purified water was gradually added to the solution while maintaining the solution at 70° C., followed by emulsification by using a conventional emulsifier. The emulsion thus obtained was cooled to 25° C. by a conventional heat exchanger, whereby a milky lotion (Example 6 of the present invention) was prepared.

What is claimed as new and desired to be secured by Letters Patent of the United States is:

1. An oil-in-water cosmetic composition, prepared by:
   (A) heating a mixture comprising
      (i) an oil selected from the group consisting of liquid paraffin, mineral oil, squalane, petroleum jelly, lower alcohol esters of fatty acids, jojoba oil, whale oil, glycerides of fatty acids, liquid acetate esters of fatty alcohols, aloe, vitamins, and mixtures thereof;
      (ii) a fat selected from the group consisting of higher fatty acids, cholesterol, cholesterol fatty acid esters, ceramides and compounds having the following formula (I):

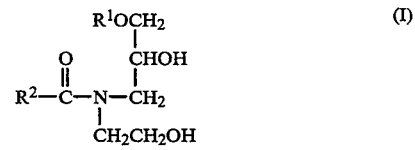

wherein $R^1$ is a linear or branched, saturated or unsaturated hydrocarbon group having 10 to 26 carbon atoms, and $R^2$ is a linear or branched, saturated or unsaturated hydrocarbon group having 9 to 25 carbon atoms, and mixtures thereof, said fat being present in at least 70 wt. % of the total of said oil and said fat;
   (iii) an emulsifying agent and
   (iv) a portion of from 0.1 to 5% of an aqueous medium selected from the group consisting of water and a combination of water and a water-soluble monohydric alcohol, at a temperature of from 60° C. to 80° C. for a length of time sufficient to provide a uniform solution; and
   (B) emulsifying said uniform solution with the balance of said aqueous medium.

2. An oil-in-water cosmetic composition according to claim 1, wherein said oil is a liquid at 25° C., and said fat is solid at 25° C.

3. An oil-in-water cosmetic composition according to claim 1, wherein fat further comprises at least one member selected from the group consisting of hydrocarbons, wax esters, glycerides of fatty acids and higher alcohols.

4. An oil-in-water cosmetic composition according to claim 1, wherein the amount of said mixture of oil and fat is from 0.5 to 20 wt. % of the total weight of said cosmetic composition.

5. An oil-in-water cosmetic composition according to claim 1, wherein the amount of said lipid is form 2 to 20 wt. % of the total weight of said cosmetic composition.

6. An oil-in-water cosmetic composition according to claim 1, wherein said emulsifying agent is a surface active agent of a polyoxyethylene alkyl ether phosphoric acid type having the following formula:

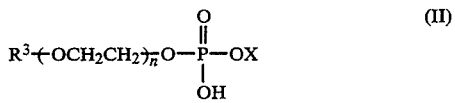

(II)

wherein

R is a hydrocarbon group of from 8 to 36 carbon atoms, n is a number of 1 to 10 on the average, and X is an inorganic or organic cation.

7. An oil-in-water cosmetic composition according to claim 6, wherein X is an inorganic cation.

8. A method for the preparation of an oil-in-water cosmetic composition set forth in claim 1, wherein said oil and said fat are a mixture, said fat being present in at least 70 wt. % of said mixture, and at least 50 wt. % of said fat is at least one lipid.

9. The composition of claim 1, wherein said ceramide is a sugar ceramide.

10. A method for the preparation of an oil-in-water cosmetic composition, comprising the steps of:

(a) mixing an oil, a fat, an emulsifying agent and a portion of an aqueous medium at a temperature of from 60° C. to 80° C., for a length of time sufficient to provide a uniform solution, said portion of said aqueous medium being from 0.1 to 5 wt. % of the amount of said aqueous medium to be included in said cosmetic composition; and (b) emulsifying said uniform solution with the balance of said aqueous medium.

11. The oil-in-water cosmetic composition of claim 1, wherein said mixture further comprises (v) from 0.5 to 10% by weight of the composition of a water-soluble polyhydric alcohol.

12. The oil-in-water cosmetic composition of claim 1, wherein said aqueous medium is water, and said aqueous medium further comprises a water-soluble polyhydric alcohol.

* * * * *

UNITED STATES PATENT AND TRADEMARK OFFICE
CERTIFICATE OF CORRECTION

PATENT NO. : 5,344,650
DATED : September 6, 1994
INVENTOR(S) : Noriko OTSUKA, ET AL.

It is certified that error appears in the above-indentified patent and that said Letters Patent is hereby corrected as shown below:

On the title page, Item [30], the Foreign Application Priority Number should read:

--2-229877--

Signed and Sealed this

Sixth Day of December, 1994

Attest:

BRUCE LEHMAN

*Attesting Officer*     *Commissioner of Patents and Trademarks*